United States Patent [19]

Helfer et al.

[11] Patent Number: 5,197,470
[45] Date of Patent: Mar. 30, 1993

[54] NEAR INFRARED DIAGNOSTIC METHOD AND INSTRUMENT

[75] Inventors: Jeffrey L. Helfer, Webster; Steven C. Switalski; Hsue-Yang Liu, both of Rochester, all of N.Y.

[73] Assignee: Eastman Kodak Company, Rochester, N.Y.

[21] Appl. No.: 568,452

[22] Filed: Jul. 16, 1990

[51] Int. Cl.$^5$ .................. A61B 5/00; A61B 17/00
[52] U.S. Cl. .................. 128/634; 128/664; 606/15
[58] Field of Search .............. 128/664, 665, 634, 633; 606/2-19

[56] References Cited

U.S. PATENT DOCUMENTS

| | | | |
|---|---|---|---|
| 3,769,963 | 11/1973 | Goldman et al. | 128/665 |
| 4,266,549 | 5/1981 | Kimura | 128/303.1 |
| 4,281,645 | 8/1981 | Jöbsis | 128/633 |
| 4,449,535 | 5/1984 | Renault et al. | 128/634 |
| 4,509,522 | 4/1985 | Manuccia et al. | 128/634 |
| 4,515,165 | 5/1985 | Carroll | 128/664 |
| 4,641,650 | 2/1987 | Mok | 128/303.1 |
| 4,655,225 | 4/1987 | Dähne et al. | 128/633 |
| 4,718,417 | 1/1988 | Kittrell et al. | 128/303 |
| 4,765,330 | 8/1988 | Bach | 128/303.1 |
| 4,800,279 | 1/1989 | Hieftje | 250/339 |
| 4,854,315 | 8/1989 | Stack et al. | 128/303.1 |

FOREIGN PATENT DOCUMENTS

| | | |
|---|---|---|
| 0214712 | 5/1986 | European Pat. Off. |
| 359433 | 3/1990 | European Pat. Off. |
| 404562 | 12/1990 | European Pat. Off. |

OTHER PUBLICATIONS

Lasers in Surgery and Medicine, vol. 9, pp. 109-116 (1989) by F. W. Cutruzzola et al.
Applied Optics, vol. 27, No. 9, (May, 1988) by A. F. Gmitro et al.

Primary Examiner—William E. Kamm
Assistant Examiner—Kevin Pontius
Attorney, Agent, or Firm—Dana M. Schmidt

[57] ABSTRACT

There are disclosed an instrument and method for using near IR to discriminate between healthy and diseased tissue, using, e.g., a catheter and a spectrophotometer. Near IR is passed at certain wavelengths to suspected tissue, and reflected light is analyzed to determine the absorbance, and preferably the second derivative thereof. From identification of the absorption spectra of known diseased and known healthy tissue, a relation has been established to determine the following correlation equation for determining the predictive value of y:

$$y = C_0 + C_1 A(\lambda_1) + C_2 A(\lambda_2)$$

wherein $A(\lambda_1) + A(\lambda_2)$ are the second derivatives for the absorbance at the two selected wavelengths. For blood cholesterol esters and plaque, $\lambda_1$ is preferably 1714.5 and $\lambda_2$ is preferably 1678.5 nm. Solving for the coefficients $C_0$, $C_1$ and $C_2$, it has been shown that values of y less than $-8.0$ represent diseased tissue, which should be treated. Ablation laser treatment is described as one mode of treatment.

20 Claims, 8 Drawing Sheets

NEAR INFRARED DIAGNOSTIC METHOD AND INSTRUMENT

FIELD OF THE INVENTION

The invention relates to an instrument and method that allow a spectrophotometer to distinguish between healthy cells and diseased cells, and also to apparatus and a method of subsequently treating the identified diseased cells.

BACKGROUND OF THE INVENTION

As has been noted in several technical journals recently, atherosclerosis is a leading cause of non-accidental death in the United States. Because the two conventional treatments, bypass surgery and balloon angioplasty, have known disadvantages, laser angioplasty is being turned to as a more effective therapeutic technique.

Even laser angioplasty has its problems, however. Chief of these is the inability to quickly distinguish between "friend" and "foe", that is, between healthy vascular tissue and the diseased plaque. Conventionally, transluminal illumination is delivered to and subsequently received from tissues, such as by diffuse reflection or direct transmission, to identify and distinguish plaque from healthy tissue. The same optics are then used to deliver therapeutic laser light to ablate diseased tissue. In the past, illumination has used light in the near UV region, and the detection has been based upon fluorescence. In some cases, the detected fluorescence was of certain fluorophors claimed to exist in the plaque. Still others are said to detect the natural fluorescence of both plaque and healthy tissue, and compare the signal with predetermined values that are said to represent healthy tissue or plaque. Such a system is described in U.S. Pat. No. 4,718,417 and in *Lasers in Surgery and Medicine*, Vol. 9, page 109-116 (1989). The latter describes the following equation to determine a so-called LIF ratio for the comparison: $LIF = Co + C_1 I_F(\lambda_1) + \ldots + C_{13} I_F(\lambda_{13})$, using 13 different wavelengths to detect the fluorescence.

In either case, there are disadvantages in such prior systems. First of all, the illumination uses near UV light, which has very low penetration power of slightly less than 100 $\mu$m thickness, "Optics of Human Skin", *Journal of Investigative Dermatology*, Vol. 77, p. 13-19 (1981). To avoid ablating the wrong (healthy) tissue, such detection techniques require the laser to also ablate only on that order. A thin layer of ablation means that the total removal time is prolonged, and more illumination and detection, and thus delay, is required to remove the same amount of diseased tissue. In any event, delays while double-checking the site cannot be easily skipped—failure to identify tissue as healthy before ablating it with laser energy can lead to vessel perforation. The risk of such perforation is considered to be "the major impediment to safe and effective laser angioplasty" in current technology, *Applied Optics*, Vol. 27, No. 9, p. 1844 (May 1988). The delay just mentioned is further aggravated when using fluorescence for detection—laser ablation light tends to dehydrate remaining plaque, which in turn can quench the fluorophore. To avoid this, an operation may have to wait up to 10-20 minutes for sufficient rehydration to occur. Such a wait is intolerable, when several ablative "blasts" are needed to get through the plaque 100 $\mu$m at a time.

Second, the inability to detect deep tissues has a further problem in that it cannot detect, until it is too late, that *all* of the vascular wall at a particular point has been converted to diseased tissue. That is, even the media tissue may be diseased, leaving only adventitia underneath it. That however can have a thickness of only 100 $\mu$m. Since the ablation removal conventionally is up to about 100 $\mu$m, the system that can "see" only less than 100 $\mu$m may end up seeing 80 $\mu$m of plaque and 20 $\mu$m of adventitia, identify it as primarily plaque, and undesirably ablate away all but 80 $\mu$m of the vascular wall.

Third, another difficulty exists in relying on fluorescence of plaque—not all plaque is homogeneous; nor do all diseased vascular tissues fluoresce. In fact, plaque has been found to contain some or all of the following: lipids, connective tissues, thrombus, necrotic tissues, mineralized deposits, smooth muscle cell tissues which have proliferated from the vessel wall, as well as other constituents. Therefore, it is very difficult to be sure the fluorescence is complete enough and specific enough to permit the simultaneous multicomponent analysis capability that is an essential prerequisite of an effective and safe "smart" laser angioplasty system. That is, many plaque constituents "look like" other healthy body tissues. For example; platelets that deposit onto the surface of an artery (such as in response to a small, naturally occurring injury in the arterial wall) can exude growth factors which will cause the healthy smooth muscle tissues of the vascular wall to grow into the arterial lumen. Such occlusive tissues are likely to look no different from those smooth muscle tissues which make up the media—the thickest element of the vascular wall. Because healthy tissues can appear in "unhealthy" states, such "diseased" tissues are very difficult to identify and discriminate from similar healthy tissues by using fluorescence.

Fourth, there occasionally arise some conditions that produce a thin surface film such as lipid deposits on the healthy tissue that *appear* to be plaque, but in fact are not because underneath the very thin film (about 50-100 $\mu$m) is healthy tissue. A discrimination system using near UV illumination and fluorescence detection can very easily misinterpret such conditions, leading to dangerous attack on healthy tissue. Such attacks can produce acute responses such as a clot. An example of such a condition follows hereinafter.

Examples of prior art patents using the near UV illumination and detection of fluorescence as described above, also include U.S. Pat. No. 4,641,650. Some such prior art techniques rely on the addition of a dye to preferentially "mark" plaque. However, dyes are inherently a systemic foreign agent, subject to risk and governmental regulation. Accordingly, dyes are to be avoided if possible.

Non-UV laser light has been used to examine tissue to identify abnormal conditions. For example, U.S. Pat. No. 4,449,535 teaches the use of a dye laser operating at a wavelength of 805 nm, the region of the very-near-infrared. The difficulty with that kind of detection system is two-fold: i) the wavelength of 805 nm is incapable of detecting two key materials of plaque in blood vessels, namely cholesterol esters and calcification, and ii) dyes for such dye lasers are not suitable for operating in wavelengths determined by the instant invention to be more appropriate for cholesterol esters and calcification.

Yet another example of the use of non-UV light for disease detection is described in U.S. Pat. No. 4,509,522. This describes the use of mid-infrared lasers operating at 5130 nm, to detect the absorption band of carbon monoxide (column 2, line 39). Such radiation is said to be carried over a fiber optic, if the exposure occurs at locations remote from the skin. This technique also suffers two disadvantages: i) the 5130 nm wavelength, although suitable for CO, is not suitable for the detection of the primary plaque components in atherosclerosis (cholesterol esters and calcification); and ii) there is no non-toxic fiber optic known to man that will transmit 5130 nm radiation.

Thus, prior to this invention there has been a need for a quick, yet accurate laser angioplasty instrument that allows for immediate identification of diseased tissue from healthy tissues before firing the laser, particularly such instrument capable of treating atherosclerosis. Such an instrument is desired for its ability to identify and discriminate between all types of diseased and non-diseased tissues, of which atherosclerosis is but one type.

SUMMARY OF THE INVENTION

We have constructed an instrument and a method that solve the above-noted problems.

More specifically, in accord with one aspect of the invention, there is provided an instrument for detecting and treating selectively, diseased portions of body tissue, the instrument comprising a) means for illuminating portions of the body tissue with light energy of predetermined wavelengths selected from the range of between about 1000 and 2500 nm, the predetermined wavelengths being effective to be selectively absorbed by a preselected component of the tissue, b) means for collecting the light at the predetermined wavelengths that is not absorbed by the tissue portions, c) means for examining the amounts of absorbance of the light by the illuminated body tissue as determined from the collected light, and d) discriminating means for discriminating one illuminated tissue component from another illuminated tissue component at the wavelengths, whereby certain illuminated portions of the body tissue are identified and located as being diseased.

In accord with another aspect of the invention, there is provided a surgical instrument suitable for atherosclerosis treatment, comprising a catheter having a distal end constructed to penetrate a blood vessel, a proximal end constructed to remain outside the blood vessel, and a body portion connecting the ends, the ends and body portion including at least one optical fiber capable of delivering from one end, illumination light of desired wavelengths, the distal end further including optical means for transmitting and receiving light energy from the fibers to a blood vessel, and from the illuminated blood vessel to the fibers, respectively; the proximal end further including a) means for generating light energy at predetermined wavelengths between about 1660 nm and about 1740 nm, b) means for delivering the generated energy to the at least one fiber, c) means for detecting the amount of such generated energy that is not absorbed by illuminated tissue in a blood vessel and d) means for discriminating illuminated healthy tissue from illuminated diseased tissue at the wavelengths, the instrument further including treating means for selectively treating only the illuminated diseased tissue as determined by the discriminating means.

In accord with yet another aspect of this invention, there is provided a method of detecting certain tissue in body tissue, comprising the steps of a) illuminating portions of the body tissue with light energy of predetermined wavelengths selected from the range of between about 1000 and about 2500 nm, the predetermined wavelengths being effective to be selectively absorbed by a preselected component of the tissue, b) collecting the light at the predetermined wavelengths that is not absorbed from the tissue portions, c) examining the amounts of absorbance of the light as determined from the collected amounts not absorbed by the illuminated body tissue, and d) discriminating one illuminated tissue component from another illuminated tissue component at the wavelengths, whereby certain illuminated portions of body tissue are identified and located.

Therefore, it is an advantageous feature of the invention that an instrument and method are provided for detecting by illumination, diseased tissue from healthy tissue, using a portion of the spectrum that is more able to penetrate tissue to determine the true condition of the tissue.

It is a related advantageous feature of the invention that such instrument and method permit treatment of identified diseased tissue in conjunction with the same instrument used for identification, at a more rapid rate than is possible using UV spectra for detection.

Although the method and instrument are particularly suited for diagnosis and treatment of atherosclerosis, it also lends itself to other disease detection as an advantageous feature.

Other advantageous features will become apparent upon reference to the following Detailed Description, when read in light of the attached drawings.

DESCRIPTION OF THE PREFERRED EMBODIMENTS

The description that follows hereinafter particularly addresses the preferred embodiment wherein atherosclerosis in all kinds of blood vessels is diagnosed and treated, using reflected wavelengths particularly effective in being absorbed by disease states of such vessels, such as plaque, and using an ablation laser for treatment. However, in determining the amount of light absorbance by the illuminated body tissue, any mode of light collection can be used. The preferred mode is reflection, in which the light used to illuminate is reflected back at the same wavelengths used to illuminate. The amount of absorbance then is the amount of reduction in amplitude that the reflected light represents, and this amount can be shown to vary characteristically with the type of tissue present. That is, when illuminating with near infrared radiation at wavelengths between about 1000 and 2500 nm, markedly different absorption curves are generated depending on whether the tissue is diseased or healthy. This is considered to be true generally, but for purposes of this invention, it will be described particularly for the identification of plaque in cardio-vascular tissue, the preferred embodiment. That is, the diseased component to be identified is preferably plaque, particularly as it is to be found in a blood vessel of any type.

Also, the preferred embodiment features the use of absorbance values at two selected wavelengths, using a spectrophotometer that examines a broad NIR range. In addition, however, a simplified spectrophotometer can be used in the invention to examine only those selected wavelengths and/or their first and second derivatives, that are found to be useful for a particular disease condition.

Figure 6:
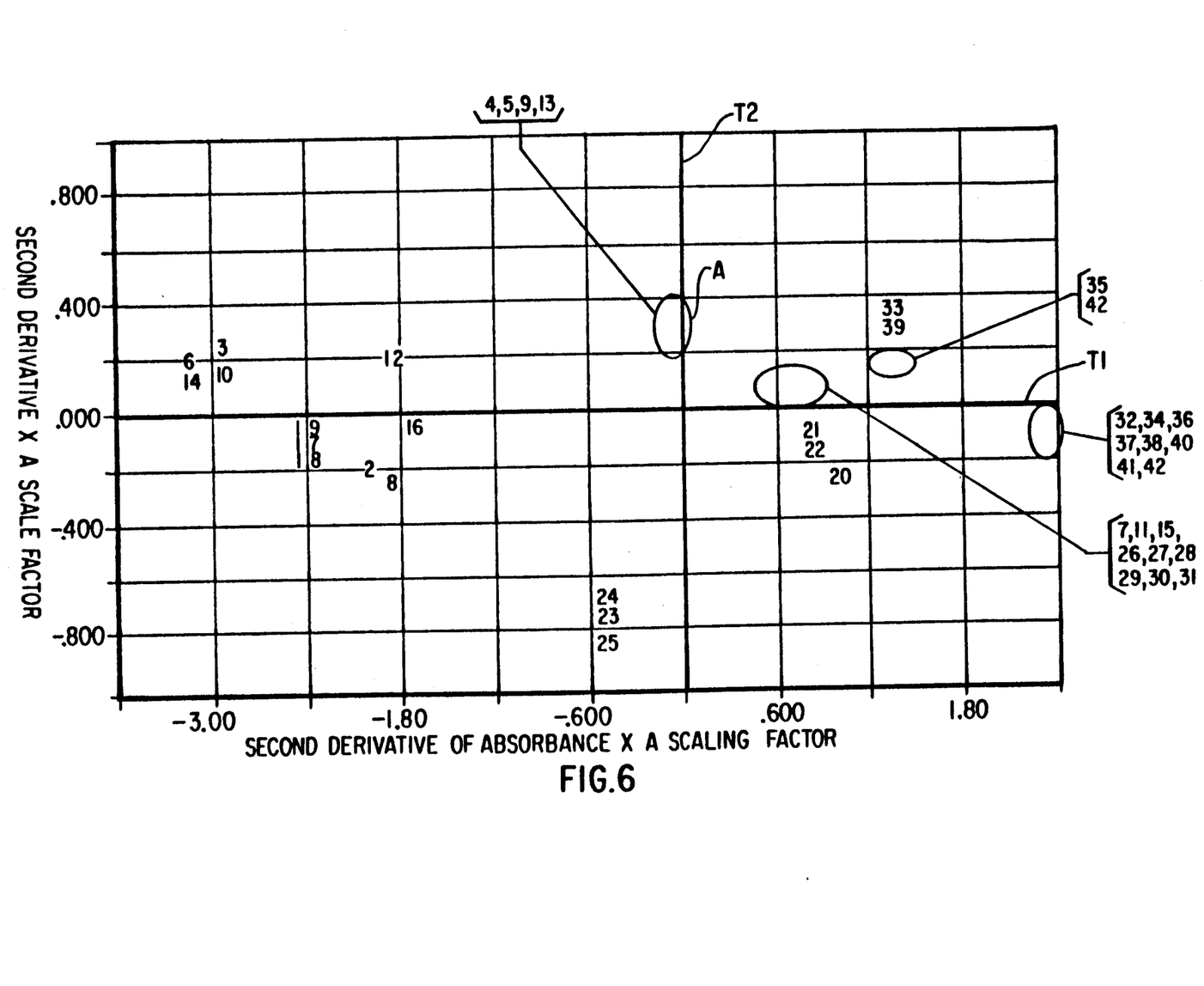
FIG. 6 is a loading plot of two principle component axes for 42 different human aorta samples.
Figure 7:
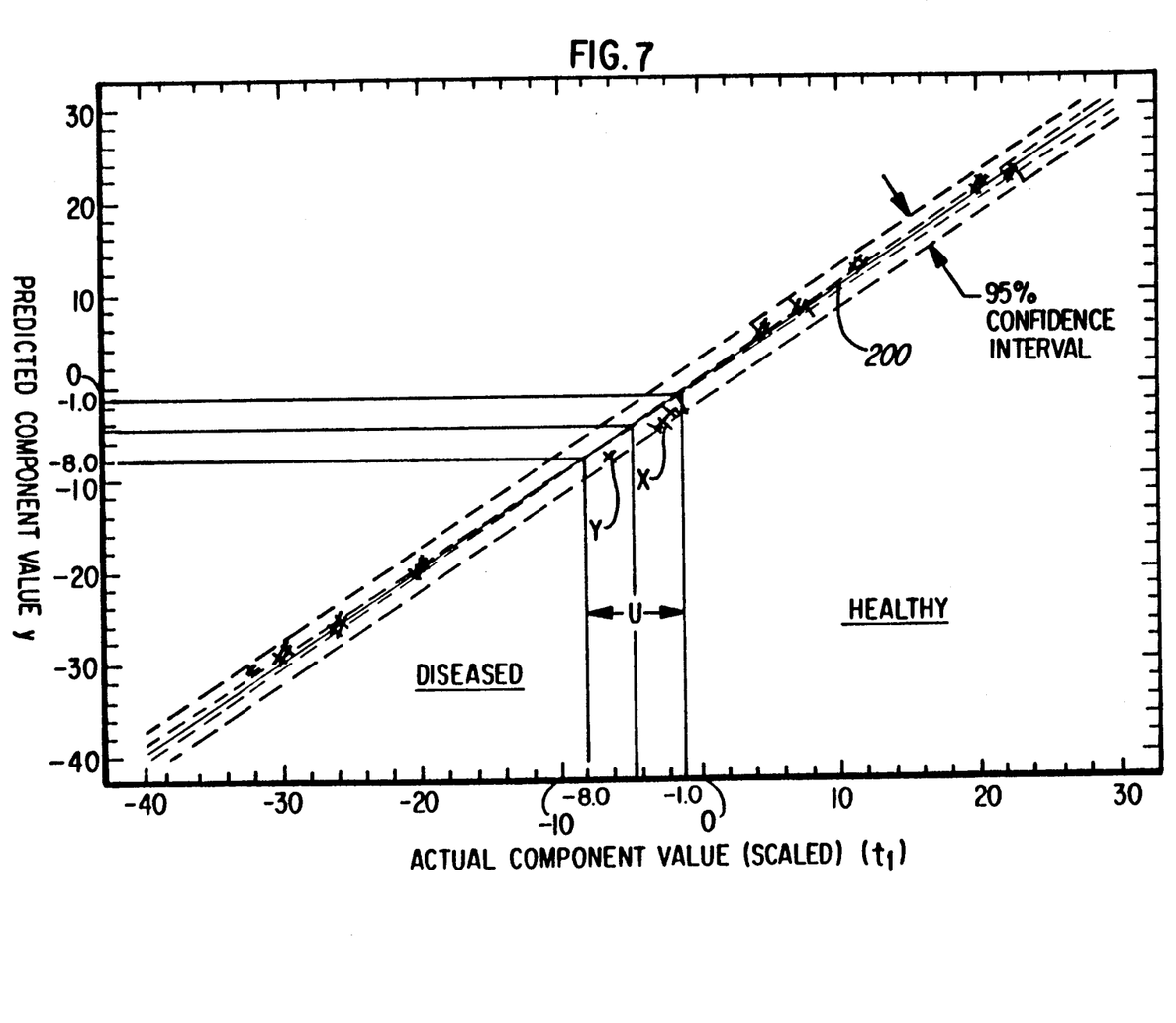
FIG. 7 is a regression plot of predicted versus actual data for distinguishing diseased versus healthy data, using two NIR wavelengths for comparison.

The more general nature of the invention is to make the discrimination between two different kinds of tissues, and more specifically, between any diseased state and the healthy tissue associated therewith. Once the diseased tissue is identified and discriminated from healthy tissue, a further aspect of the invention, which is nevertheless optional, is to treat that diseased tissue. Any mode of treatment is suitable, but only laser ablation, the preferred embodiment, is discussed herein. If the disease condition is something other than plaque, it is a simple matter to scan the diseased tissue of choice, and detect the near IR that is reflected to determine the characteristic wavelengths that are peculiarly different, in their absorption, from the wavelengths absorbed by the healthy tissue. The principle component analysis procedure and multiple linear regression hereinafter described, e.g., for FIGS. 6 and 7, is applied for, e.g., a number of selected wavelengths suited to this disease, within the range of 1000 to 2500 nm, and an uncertainty zone (FIG. 7) is plotted as has been done hereinafter, but based upon the wavelengths suited to this particular disease.

Figures 1A, 1B:
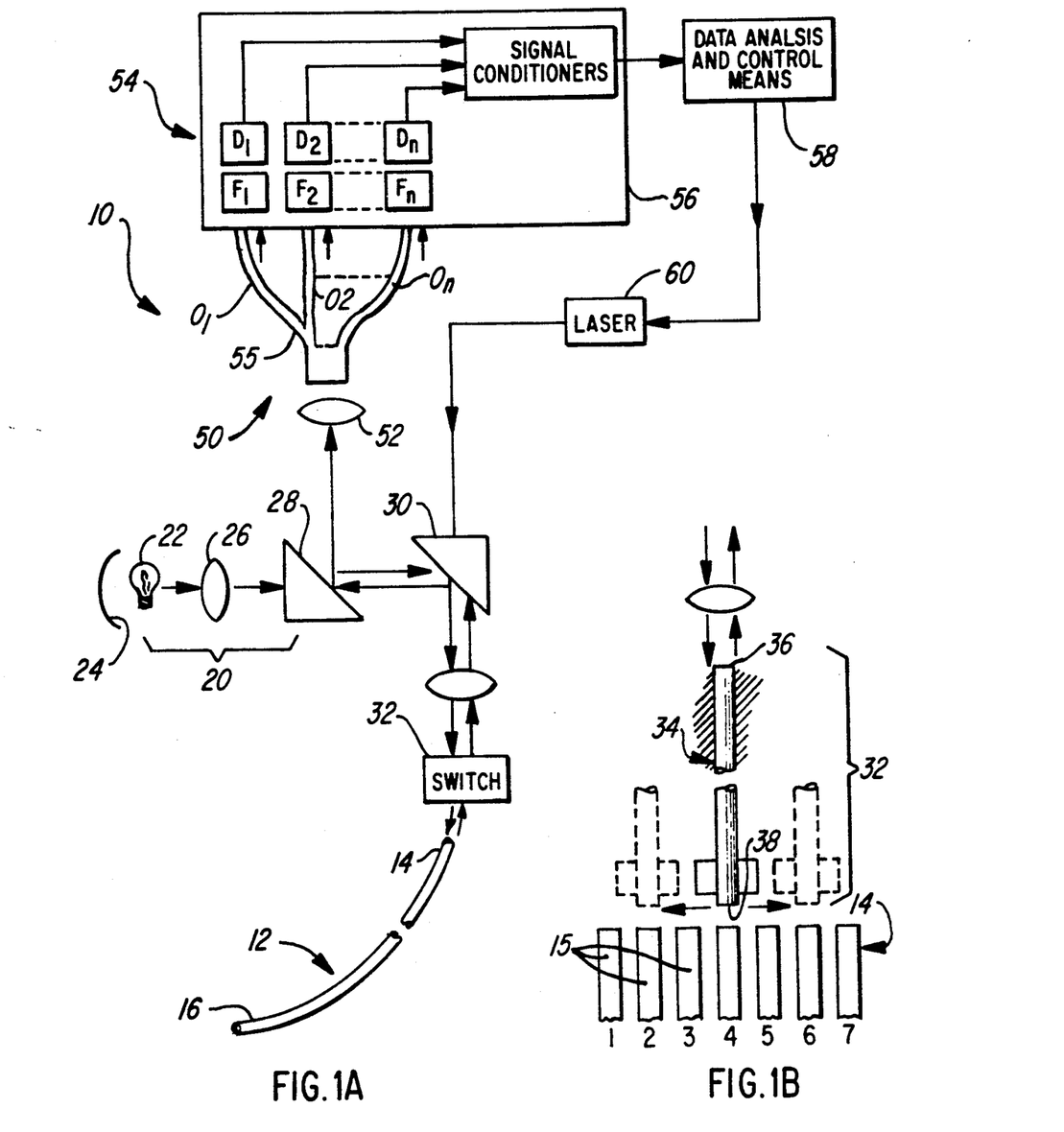
FIG. 1A is a fragmentary, partially schematic illustration of the instrument of the invention.
FIG. 1B is a fragmentary, partially schematic enlarged illustration of the switch of FIG. 1A.

Referring now to FIG. 1A and 1B, an instrument 10 constructed in accord with the invention comprises a catheter 12 to be placed into a patient body, e.g., an artery, a light source portion 20, a detector portion 50, control means 58 and a laser 60. Catheter 12 has proximal portion 14 comprising a plurality of several, e.g. 7, optical fibers 15, carrying light to a distal end 16 (described hereafter) and returning reflected light to portion 50.

Light source portion 20, FIG. 1A, can feature any convenient source of radiation, selected to include significant radiation in the range of from 1000 to 2500 nm. For example, it can comprise a lamp 22, reflector 24, optical focusing elements 26 and a beam splitter 28, so that the light image reflects off a second beam splitter 30 through a switch 32 to illuminate individual fibers 15 of catheter 12, FIG. 1B.

Switch 32 is an optical switch, which conventionally provides an intermediate fiber optic 34 that is anchored at one end 36, with an opposite end 38 that is magnetically moved rapidly to the various positions, shown in phantom, that align with ends 14 of fibers 15. Such a switch is available from York.

Detector portion 50 comprises a lens 52, n optical fibers 55 carrying n bifurcated beams $O_1, O_2 \ldots O_3$ from lens 52, and a spectrophotometer 56. Inside the spectrophotometer is a set of n filters $F_1, F_2 \ldots F_n$ and a corresponding set of n photodetectors 54, for scanning each of the optical fibers of catheter 12 at the wavelengths selected by filters $F_1, F_2 \ldots F_n$. Suitable photodetectors include germanium, lead sulfide, lead selenide or indium galium arsenide detectors. The value of n for the detectors, filters, and fibers 55 is dependent on the number of wavelengths needed, as discussed hereinafter. If $n >> 19$, then the filters preferably are replaced with a dispersive device such as a grating or prism, as in a monochromator or spectrograph.

Any spectrophotometer 56 is useful for this purpose. The output of spectrophotometer 56 is analyzed by control means 58, that includes computing means of any suitable type to do the numeric analysis described below and to solve an equation, noted hereinafter. Control means 58 in turn provides a control signal to laser 60, to fire a laser beam along any one of the optic fibers 15 that is determined to be viewing a diseased site, but only along such fibers. Switching mechanism 32 is used to switch the laser to an appropriate fiber, which can be the same switching mechanism as described for illuminating each of the optic fibers 15 with light from source 22.

Figure 2:
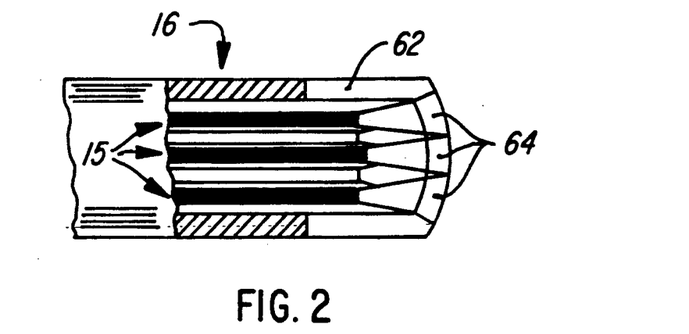
FIG. 2 is a fragmentary elevational view, partially in section, of the distal end of the catheter.

As shown in FIG. 2, distal end 16 comprises a transparent shield 62 adjacent the focusing ends 64 of fiber optics 15. Such ends deliver a cone of light, 70, FIG. 3, that is divided into separate cones $72a, 72b, \ldots$ up to $72m$, or m cones for m fibers. Preferably, $m=7$. Laser light for treatment also is confined to each cone $72a$, etc. but the depth of treatment can be, and preferably is, less deep, as shown by the shaded portion. Thus, for the NIR range of 1000 to 2500 nm, penetration depth for examination is from about 1 mm to about 5 mm, whereas treatment depth is preferably from about 5 μm to about 100 μm. However, treatment depth can be linearly scaled as described hereafter.

Figure 3:
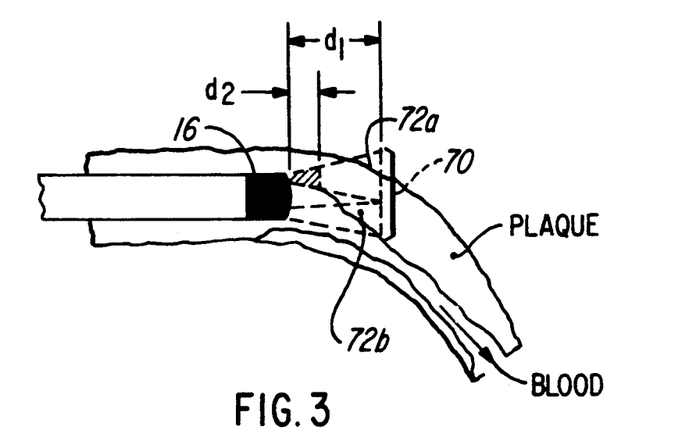
FIG. 3 is a fragmentary elevational view of such distal end in an artery, illustrating its manner of use.

The same cones of emitted light $72a \ldots 72m$ represent the tissue that reflects back the emitted light, except to the extent it is absorbed.

Preferably control means 58 uses a disease index equation regressed to fit large numbers of patient data so as to be predictive from the absorbance, or the first or second derivative of absorbance, at the minimum number of wavelengths within the range of 1000 to 2500 nm, needed to discriminate tissue. That is, a spectrophotometer 56 can read absorbance at wavelength data points adjacent to each of the preferred wavelengths, to allow a first and/or a second derivative to be calculated and compared against a threshold value. Thus, a useful disease equation index, is preferably of the form $$y = C_0 + C_1 A(\lambda_1) + C_2 A(\lambda_2) + \ldots C_n A(\lambda_n) \quad (1)$$

where $A(\lambda_i)$ is the absorbance, or the first or second derivative of the absorbance, depending upon the confidence levels of the raw data—that is, how likely is it that a particular spot illuminated by the catheter is totally healthy, or totally diseased. The value of n is determined as the minimum number needed to assure accurate and reliable prediction. This in part depends upon the aperture of the illuminating beam and thus the area of the tissue examined. The larger the area, the less likely it is that the tissue is *totally* healthy or unhealthy. Thus, if the diameter of the area viewed is no larger than about 100 μm, it is believed that it is likely that $A(\lambda_i)$ can be just the raw absorbance, instead of a derivative, if there is no baseline shift.

Figure 4:
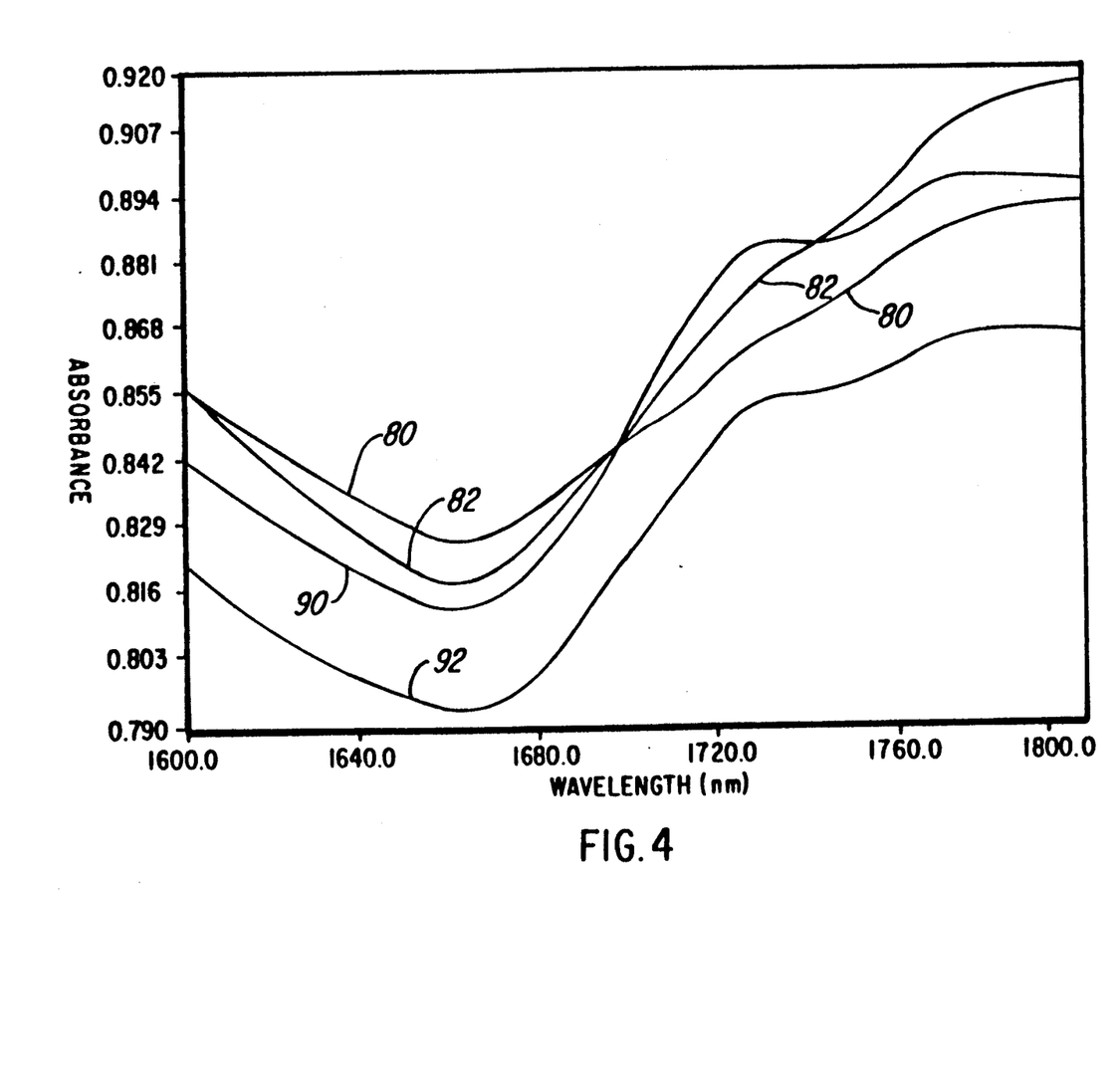
FIG. 4 is an absorbance plot representative of the absorbance obtained by the spectrophotometer of the invention, of four different samples of human aorta, viewed ex vivo.
Figure 5:
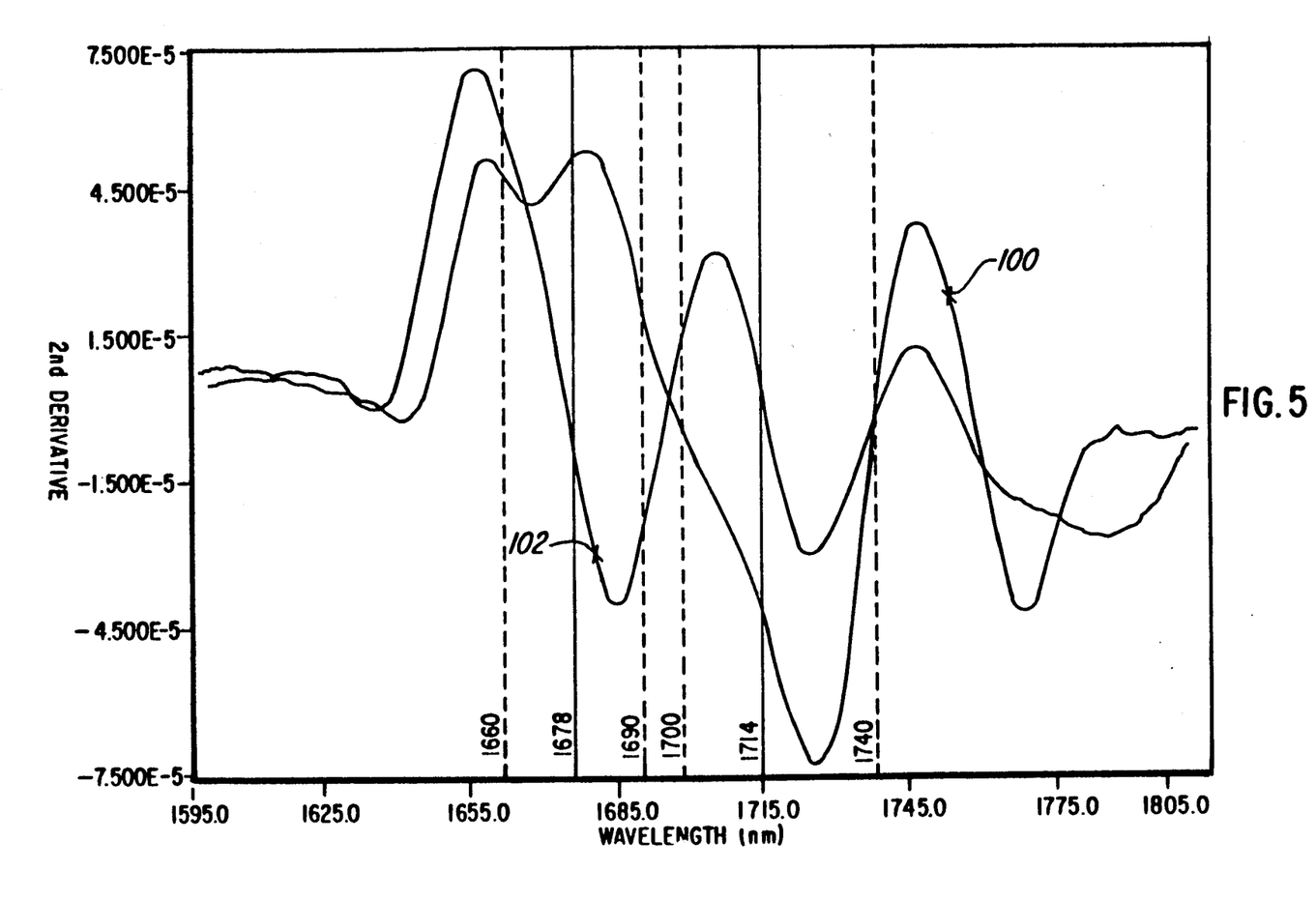
FIG. 5 is a plot of the second derivative of absorbance for two different human aorta samples.

Referring again to Equation (1), this equation has been derived as follows:

The absorbance of a large number of healthy and diseased tissues is plotted against a continueum of wavelengths between the values of 1000 and 2500 nm. The example charted in FIG. 4 shows only four such curves, where 80 and 82 are healthy tissue of a blood vessel, and 90 and 92 are from diseased tissue characterized as plaque. Because each sample can have a baseline shift that is extraneous to the characteristic absorbance, the first and second derivative is preferably taken for all the data. FIG. 5 illustrates an example of the second derivative taken from the absorbances of aorta from only two different human patients. Curve 100 is a disease curve (representing plaque), and curve 102 is a healthy curve. It will be readily apparent that the region between cross-over points is particularly useful, but only where the curves are widely divergent. From the graph of FIG. 5 it is apparent that this defines the region of from about 1660 nm to about 1690 nm, and then from about 1700 nm to about 1740 nm, or more broadly, from about 1690 nm to about 1740 nm. Even the region of 1690–1700 is useful, unless it turns out to be the cross-over point for *all* the data being considered, which is not the case for plaque in human aorta.

Next, numerical analysis is done via the standard technique of "principle component analysis" (PCA) as described, for example, in "The Use of Principal Components in the Analysis of Near-Infrared Spectra", Cowe et al, *Analytical Chemistry*, Vol. 39 (1985), pp. 257-266.) Such a process involves plotting values of the absorbance, or the first or second derivatives of the absorbance measured at, or calculated for, for example, two wavelengths, in at least two and up to n dimensional space, using known PCA mathematics to determine the representative axes of greatest variance in the values (hereinafter, data points). As a result, principle components axis $T_1$ is the axis of the greatest variation in the data, regardless of the cause of that variation. Axis $T_2$ is chosen, FIG. 6, to represent the next greatest axis of variation, and typically represents some variance factor other than that plotted on $T_1$.

The purpose of the exercise is to determine a) what wavelengths, if any, correlate to a maximum distinction between tissue samples, and b) whether such distinctions correlate to disease conditions. In FIG. 5, one can see that a plausible set of Lambda's would be, e.g. 1678 nm and 1714 nm. However, because many samples and many curves are required to pick the best wavelengths, the human eye cannot readily identify the best wavelengths. Instead, when the $T_1$ scores from the PCA analysis are obtained, a new plot, FIG. 7, is prepared. Multiple linear regression on all the sample spectra, using the $T_1$ scores as input data and using a 95% confidence limit, provides a fit to the data. The predicted values are shown on the y-axis. For plaque in human aorta, n of $\lambda_n$ need only be equal to 2. Using this data, the equation is solved to determine the coefficients, and the equation then for line 200 is found to be:

$$y = -158.77 - 3.72 \times 10^6 A(\lambda_1) + 2.03 \times 10^6 A(\lambda_2), \quad (2)$$

for $\lambda_1 = 1714$ nm and $\lambda_2 = 1678$ nm.

Next, all the samples used in analysis are examined by a skilled pathologist, to determine which samples are healthy and which are diseased. For plaque in a blood vessel, containing cholesterol esters and calcification as the primary distinguishing components, we have found that the graph of FIG. 7 is in fact a plot discriminating diseased from healthy tissue. Stated in other words, the principle component axis $T_1$ has been found to be distinguishing the samples based upon whether or not they are diseased, as the primary distinguishing feature.

From this discovery, we have ascertained a threshold value of y which is a predictive of diseased conditions. That value in FIG. 7 has been found to be any value of y less than $-8.0$. Thus, the instrument of this invention determines that plaque is present if and when the instrument determines that $y \leq -8.0$, using only the second derivatives of two wavelengths being read, for example, 1714 and 1678 nm. Both equation (2) and the threshold value of $-8.0$ are stored in control means 58.

It will be seen that there is a range, marked U for "uncertainty", FIG. 7, of values "y" that is not predictive either way. Such values occur due in part to the ability of the near infrared to penetrate through to healthy underlying tissues, FIG. 8, unlike UV or visible diagnostic radiation used in the prior art. The actual boundaries for zone U were determined as follows: during the examination of the tissue samples, it was determined that the bunch of "healthy" samples that is closest to the closest diseased samples (Y) was bunch X. These two bunches were bisected, which produces a Y value of about $-4.5$. The highest boundary for zone U was picked as that value just above healthy bunch X, namely a Y value of about $-1.0$, and the same value of that increment (3.5) was then subtracted from the bisecting value of $-4.5$ to produce the other boundary $-8.0$.

Regarding the values on the y-axis of FIG. 7, the relative scale results from the difficulty in defining and quantifying what is a "diseased state" of the tissue. If a clear and descriptive definition of disease could be agreed upon, and if a method could be found for extracting the disease components and quantifying them (percent weight or other form of chemical concentration), then the y-scale could be made absolute. The method proposed for using near IR wavelengths for tissue discrimination described herein would remain the same, except that one would use the absolute y-scale. In absence of such definitions and data, however, the use of expert pathology and principle component analysis has allowed for a relative scale which can function to provide the advantages noted herein.

Regarding the treatment that is applied to the identified diseased tissue, a variety of treatments are possible and conventional. Any such treatment known to be done via a catheter is useful with this invention. Preferred is surgical removal of the tissue, and most preferred is laser ablation.

Optionally, auxilliary features can also be included on the catheter (not shown). For example, the catheter can include expandable balloons either for positioning or treatment.

Regarding laser ablation, a wide variety of lasers 60 can be coupled to the optics of the laser to perform such ablation. Such lasers are well-known and detailed descriptions are not needed. The selection will depend partly on the desired result. For example, pulsed 308 nm xenon chloride excimer lasers can be used, and have been described, for example, in "Laser Ablation of Human Atherosclerotic Plaque," *J. Am. Coll. Cardiol.*, Vol. 5, pp. 929-933 (1985). Such a laser can be operated to remove 17 μm of tissue per pulse.

Other useful lasers include any others that are heavily attenuated by tissues, such as Er:YAG or Holmium-:YAG.

Figure 9:
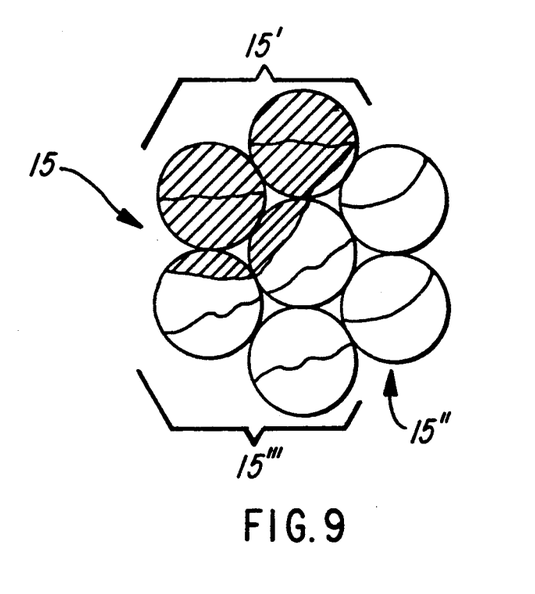
FIG. 9 is a representative schematic illustration of the reflection spectra that is carried by fibers 15 of the catheter used by this invention.

The method of the invention will be readily apparent from the preceding. In brief, catheter 16, FIG. 1, is inserted into the patient's body at a suitable site, and fed along the cardiovascular system to a suspected site. At the suspected site, the light source of portion 20 is cycled through each of the optic fibers 15 to illuminate that spot, FIG. 3. Simultaneously, reflected light passes out each of fibers 15 when each fiber is switched sequentially to detectors 54, FIG. 1. Each of these fibers 15 will deliver a spectrum of absorption controlled by filters $F_1, F_2 \ldots F_n$, within the range of 1000 to 2500 nm, as shown in FIG. 9. Some of these will reflect light from the blood itself (group 15'), some from healthy tissue (group 15''), and some from diseased, or plaque tissue (group 15'''). Control means 58, FIG. 1, then specifically examines the absorption at the selected wavelengths, e.g., $\lambda_1$ and $\lambda_2$, which for FIG. 7 are 1678 and 1714. From this the second derivative is calculated for $\lambda_1$ and $\lambda_2$. The value of y in equation (1) is then calculated, and in the case of plaque and cholesterol esters, if that value is less than $-8.0$, for a given fiber 15, then laser 60 is fired either automatically or by manual operation to ablate away the diseased tissue.

As noted above, it is unlikely that the plot of FIG. 5 represents any true cross-over point, since only two curves are shown, out of the 42 samples actually used to produce FIGS. 6 and 7. However, in the event crossover point 1740 nm were found to be stable and valid for all 42 curves, that point can be used to calibrate the instrument.

Uncertainty region U of FIG. 7 has usefulness in the practice of the invention, since the instrument must be able to detect conditions where plaque has consumed most of the wall of the blood vessel. In the condition shown in FIG. 8, blood vessel 210 is defined by endothelial layer 212 between which blood flows, arrow 213, with plaque deposits such as deposit 214 existing on layer 212. Under layer 212 is intima layer 216, and below that, media layer 218. In this example, plaque has built up to almost completely fill layer 218, at region 220. Below layer 218 is the adventitia layer 222, and below that, fat 224.

Figure 8:
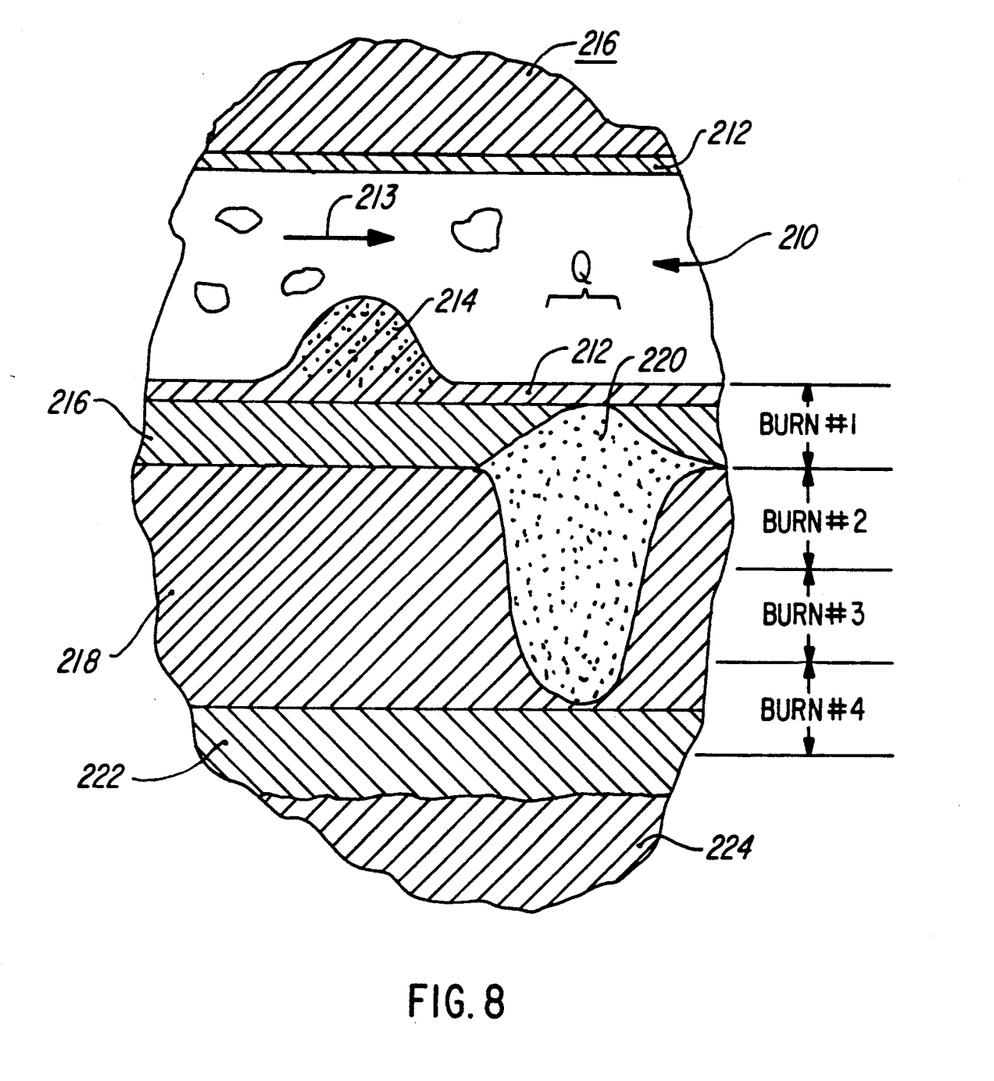
FIG. 8 is a fragmentary schematic section view of an artery that can be diagnosed and treated in accordance with the invention, the sectioning of which is intended to represent tissue.

The instrument of this invention is able to detect the adventitia layer 222 underneath the plaque, and deliver a signal that is part healthy and part diseased, thus falling within region "U" of FIG. 7. This will force the instrument to timely cease laser ablation, even though plaque remains as the form of the media at region Q. In contrast, UV/visible diagnostic instruments will not detect the adventitia layer 222 underneath the plaque, and will keep firing until all the plaque is gone. Unfortunately the last ablation step ("burn" #4) will be likely to ablate too far through the adventitia, thus perforating the vessel. In contrast, however, after "burn" #3, or even after "burn" #2 is done with this invention, the diagnostic phase of this invention will detect enough of the healthy tissue of layer 222 underneath, as to place the "y" values of equation #1 in the "uncertainty" region U, and no more laser treatment will be done, thus avoiding perforation of the blood vessel. (The use of the term "burn" in FIG. 8 is a short-hand reference to the ablation that occurs. Strictly speaking, no burning of the tissue is desired or occurs, but rather ablation.)

Still further, the dosage value of the laser exposure, that is, both the power and the length of the ablation, is preferably adjusted depending upon how far away the value of "y" is, FIG. 7, compared to the threshold ($-8.0$ in the above example.) Maximum dosage is assigned to $-40$, and it can be scaled back linearly to zero at $-8.0$.

Figure 10:
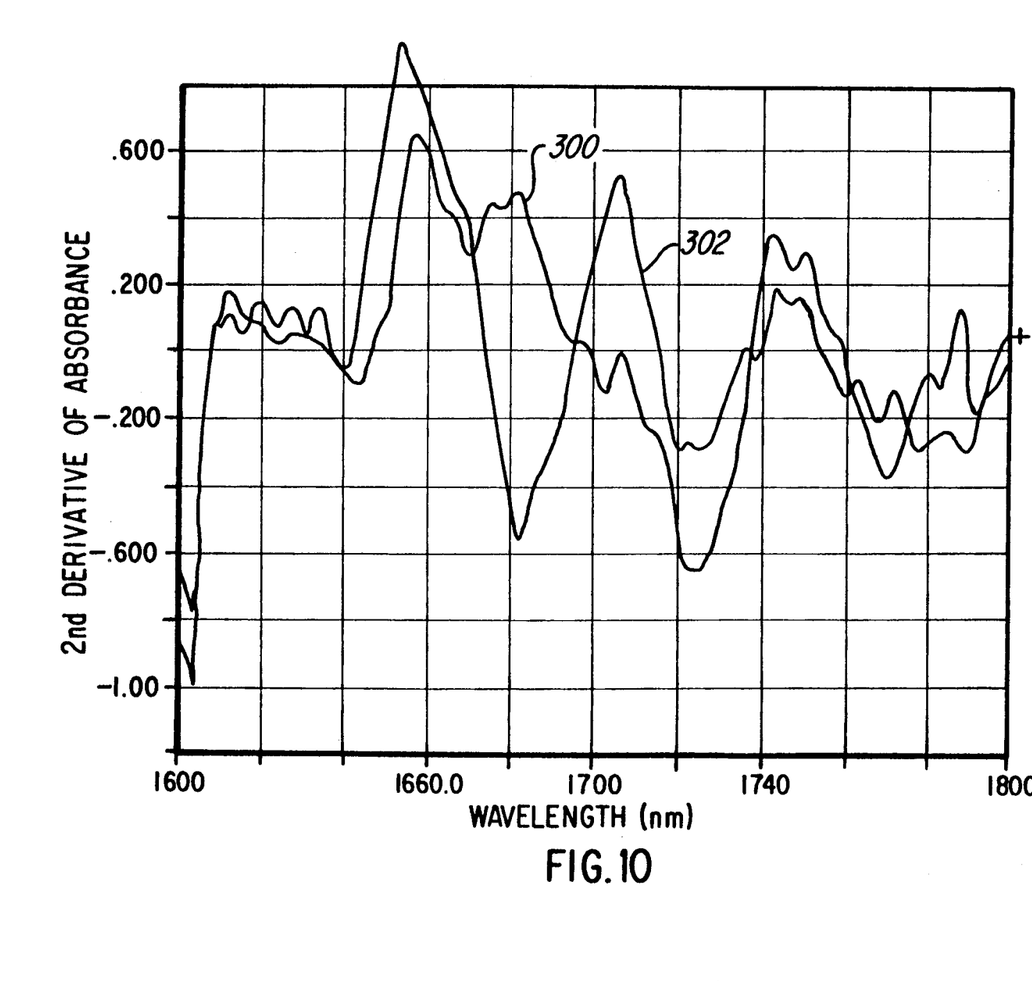
FIG. 10 is a plot similar to that of FIG. 5, but illustrating different results for a different sample.

FIG. 10 is a further illustration of a use of the invention. This plot shows curves 300 and 302, of which 300 is diseased. The question is, curve 302. The importance of this curve is that, visually, the aorta involved had the appearance of being diseased. However, it turned out this was superficial only, due to a thin layer of lipids. Underneath, this aorta was perfectly healthy, as was confirmed by the application of equation (1), examination of curve 302 and the plot of FIG. 7, where y was about 12. The reason of course was the ability of the NIR to penetrate the lipid layer (of only about 50-100 nm) to determine that, underneath, the tissue was very healthy. This detection would NOT have been possible using only UV/visible illumination and detection.

EXAMPLES

The following examples are illustrative only of the procedure used to practice this invention.

The condition of all of the data of the plot of healthy versus diseased samples that comprise FIGS. 6 and 7 was determined by a pathological review of samples as follows:

EXAMPLE 1

Four Samples from Patient #1

Four aorta samples, one square inch in size each, were submitted in 10% buffered formalin for microscopic evaluation. A gross pathologic report with age, cause of death, and description of lesions was not available.

The samples were labeled as 1A, 1B, 1C and 1D. The above specimens were kept in buffered formalin for seven days before trimming. Samples of each specimen were trimmed to reveal a cross section of the arterial wall. Tissue samples were processed by routine histologic techniques and examined microscopically.

The samples were described in the increasing order of severity of lesions. All samples contained a variable number of bacterial colonies, but their number and location were not recorded because their growth probably occurred after death.

1A. Intima: The intima comprised only approximately 1/6 of the aorta wall. The majority of the cross section contained hyalinized collagenous fibers, extracellular matrix, and few myointimal cells separated by minor edema.

Media: This layer comprised approximately 4/6 of the aorta wall. It contained amorphous ground substance (probably proteoglycans), concentrically arranged laminae of elastic tissue, and intervening smooth muscles.

Adventitia: This layer comprised approximately 1/6 of the aorta wall. It consisted of a large number of adipose tissue cells, some elastic fibers, and a few thin-walled nutrient vessels (vasa vasorum).

1C. Intima: The thickness of the intima increased to approximately 2/6 of the aorta wall. The extracellular matrix and hyalinized collagenous fibers accounted for all of increase in the thickness of this layer. The number of myointimal cells was unchanged when compared to 1A sample.

Media: The thickness of this layer comprised about 3/6 of the aorta wall. Microscopically it was similar to the corresponding layer of 1A. In addition, there were few small accumulations of red blood cells separating elastic fibers.

Adventitia: The thickness of this layer comprised approximately 1/6 of the aorta wall. The microscopic appearance was similar to the corresponding layer of 1A.

1D. Intima: This layer comprised about 3/6 of the aorta wall. One complete and one incomplete atheromatous plaque were present on the section. On the luminal side the plaques were covered by a fibrous cap consisting of dense layers of hyalinized collagenous fibers, fibrin-like strands, and amorphous eosinophilic material. The center of the plaque contained crystals of cholesterol esters, fibrin-like structures, and granular and amorphous eosinophilic material.

Media: The media comprised about 2/6 of the aorta wall. Microscopically, it was similar to the corresponding layer of 1A.

1B. Intima: The thickness of this layer comprised about 3/6 of the aorta wall. It contained a single ulcerated atheromatous plaque. The remnants of the fibrous cap were folded back over the adjacent endothelium. The crater-like center of the plaque, comprised of crystals of cholesterol esters and granular and amorphous eosinophilic substance, became part of the aortal lumen. In addition, few macrophage-like cells, hemosiderin-like pigment, and two small groups of red blood cells were present in the plaque. Intima that was adjacent to the plaque consisted of hyalinized collagen fibers, a few atrophic muscle fibers, fibrin-like structures, and amorphous eosinophilic material.

Media and Intima: The media and intima comprised approximately 2/6 and 1/6 of the aorta wall respectively. Microscopically, they were similar to the corresponding structures of the 1A.

The conclusion was, sample 1A was healthy albeit with fatty deposits, 1B was diseased, 1C was healthy, and 1D was diseased.

EXAMPLES 2 AND 3

Multiple specimens, five from patient #2 identified as A, B, C, D and E and three from patient #3 identified as A, B and C, on square inch in size each, were submitted in 10% buffered formalin for microscopic evaluation.

Information on age, cause of death and description of lesions was not submitted with the specimens.

The above specimens were kept in buffered formalin for seven days before trimming. Each specimen was trimmed to reveal on cross section of the arterial wall. Tissue specimens were processed by routine histologic techniques and examined microscopically.

All specimens contained a variable number of bacterial colonies, but their number and location were not recorded because their growth probably occurred after death.

Specimens 2A and E

Intima: The intima comprised approximately 2/6 of the aorta wall. The majority of the cross section contained hyalinized collagenous fibers, extracellular matrix, and a few myointimal and mononuclear cells. Dystrophic calcification was spread throughout the intima and ranged in size from small foci to a large plaque involving the entire thickness of the intima. Each plague was covered by thick fibrous cap.

Media: This layer comprised approximately 3/6 of the aorta wall. It contained amorphous ground substance, concentrically arranged laminae of elastic tissue, intervening smooth muscles, and a few scattered macrophages.

Adventitia: This layer comprised approximately 1/6 of the aorta wall. It contained irregularly arranged collagen and elastic fibers, and a few nutrient vessels.

The fibrous cap over the calcified plaque in specimen 2E was torn during the processing.

Specimens 2B, C and D

Intima: The intima comprised approximately 2/6 of the aorta wall. The majority of the cross section contained hyalinized collagenous fibers, extracellular matrix, and a view myointimal cells.

Media: This layer comprised approximately 3/6 of the aorta wall. It contained amorphous ground substance, concentrically arranged laminae of elastic tissue, intervening smooth muscles, and a few scattered macrophages.

Adventitia: This layer comprised approximately 1/6 of the aorta wall. It contained irregularly arranged collagen and elastic fibers, and a few nutrient vessels.

Specimens 3A, B and C

Intima: This layer was comprised entirely of the endothelium.

Media: The media comprised 2/6 to 4/6 of the aorta wall. It contained amorphous ground substance, concentrically arranged laminae of elastic tissue, intervening smooth muscles, and a few scattered macrophages.

Adventitia: The thickness of this layer grew progressively from A to B to C. This layer comprised from 2/6 to 4/6 of the aorta wall. It consisted of large numbers of irregularly arranged collagen fibers, elastic fibers, adipose tissue cells, chronic inflammatory cells, and few nutrient vessels. The majority of increase in the thickness was attributable to an increase in the number of collagen fibers. In the B sample, there was a single accumulation of about 100 lymphoblastoid cells wedged between the collagen fibers.

Hence, the conclusions were as follows:
2A—diseased
2B—healthy
2C—healthy
2D—healthy
2E—diseased
3A—healthy
3B—healthy
3C—healthy

Regression

All of the samples of Examples 1–3 were then correlated in the plots of FIGS. 6 and 7, along with some additional samples to total 42 in all, to establish that the distinguishing factor is in fact the extent of disease present. The resulting equation of $$y = -158.77 - 3.72 \times 10^6 A(\lambda_1) + 2.03 \times 10^6 A(\lambda_2)$$

was obtained, where $A(\lambda_1)$ is the second derivative of the NIR absorbance at 1714 nm, and $A(\lambda_2)$ is the second derivative of the NIR absorbance at 1678 nm.

Although only two wavelengths have been shown to be sufficient to distinguish plaque from healthy aorta tissue, such a minimum may not apply to other diseased states. That is, plaque can be characterized by a few chemical components, primarily cholesterol esters and calcification. If another diseased state is controlled by, say five components, or more details are desired, many more than two wavelengths may be necessary.

The invention has been described in detail with particular reference to certain preferred embodiments thereof, but it will be understood that variations and modifications can be effected within the spirit and scope of the invention.

What is claimed is:

1. An instrument for detecting diseased portions of body tissue, said instrument comprising
   a) means for illuminating portions of said body tissue with light energy of predetermined wavelengths selected from the range of between about 1000 and 2500 nm, said predetermined wavelengths being effective to be selectively absorbed by a preselected component of said tissue,
   b) means for collecting the light at said predetermined wavelengths that is not absorbed by said tissue portions,
   c) means for determining from said collected light the amounts of absorbance of said light by illuminated body tissue, and
   d) discriminating means for discriminating one illuminated tissue component from another illuminated tissue component at said wavelengths,
   said discriminating means comprising i) means for converting said absorbance amounts into first or second derivative values, ii) storage means for storing a disease index equation, iii) means for solving this equation using said first or second derivative values to produce a disease index value, and iv) comparing means for comparing said disease index value against a threshold value for diseased and healthy conditions of said tissues,
   whereby certain illuminated portions of the body tissue are identified and located as being diseased.

2. An instrument for detecting diseased portions of body tissue, said instrument comprising
   a) means for illuminating portions of said body tissue with light energy of predetermined wavelengths selected from the range of between about 1000 and 2500 nm, said predetermined wavelengths being effective to be selectively absorbed by a preselected component of said tissue,
   b) means for collecting the light at said predetermined wavelengths that is not absorbed by said tissue portions,
   c) means for determining from said collected light the amounts of absorbance of said light by illuminated body tissue, and
   d) discriminating means for discriminating one illuminated tissue component from another illuminated tissue component at said wavelengths, said discriminating means i) using the equation $$y = C_0 + C_1 A(\lambda_1) + C_2 A(\lambda_2) + \ldots C_n A(\lambda_n)$$

wherein $A(\lambda_1)$, $A(\lambda_2)$ and $A(\lambda_n)$ are the absorbances or the first or second derivatives of the absorbances of said tissue at n predetermined wavelengths, and $C_0$, $C_1$, $C_2$ and $C_n$ are predetermined constants, and ii) comparing the calculated y value against a predetermined threshold value.

3. An instrument as defined in claim 1 or 2 and further including
   e) means for treating only the identified and located tissue portions.

4. An instrument as defined in claim 1 or 2 wherein said illuminating means include light-energy generating means for generating said predetermined wavelengths, and at least one optical fiber for transmitting said wavelengths.

5. An instrument as defined in claim 1 or 2 wherein said illuminating means selectively illuminate at a plurality of wavelengths selectively absorbed by disease components of choice of said tissue, and said discriminating means discriminates diseased tissue from healthy tissue.

6. An instrument as defined in claim 5 wherein said wavelengths are selectively absorbed by cholesterol esters and said body tissues are cardiovascular tissues.

7. An instrument as defined in claim 6 wherein said wavelengths are selected from between about 1660 nm and about 1740 nm.

8. A surgical instrument suitable for atherosclerosis treatment, comprising a catheter having
   a distal end constructed to penetrate a blood vessel,
   a proximal end constructed to remain outside the blood vessel,
   and a body portion connecting said ends,
   said ends and body portion including at least one optical fiber capable of delivering from one end, illumination light of desired wavelengths,
   said distal end further including optical means for transmitting and receiving light energy from said fibers to a blood vessel, and from the illuminated blood vessel to said fibers, respectively;
   said proximal end further including a) means for generating light energy at predetermined wavelengths between about 1660 nm and about 1740 nm, b) means for delivering said generated energy to said at least one fiber, c) means for detecting the amount of such generated energy that is not absorbed by illuminated tissue in a blood vessel, and d) means for discriminating illuminated healthy tissue from illuminated diseased tissue at said wavelengths,
   said discriminating means comprising i) means for converting said absorbance amounts into first or second derivative values, ii) storage means for storing a disease index equation, iii) means for solving this equation using said first or second derivative values, to produce a disease index value and iv) comparing means for comparing said disease index value against a threshold value for diseased and healthy conditions of said tissues.

said instrument further including treating means for selectively treating only the illuminated diseased tissue as determined by said discriminating means.

9. An instrument as defined in claim 8, wherein said predetermined wavelengths generated by said light-energy generating means comprise wavelengths that are absorbed by at least some of the components of deposits that are not present in healthy blood vessel tissue.

10. An instrument as defined in claim 8, wherein said predetermined wavelengths are $1678 \pm 20$ nm and $1714 \pm 20$ nm.

11. An instrument as defined in claim 8, wherein said treating means comprise an ablating laser and switching means operatively connecting said ablating laser to said at least one fiber only when said fiber is illuminating diseased tissue as determined by said discriminating means.

12. A method of detecting certain tissue in body tissue, comprising the steps of
   a) illuminating portions of said body tissue with light energy of predetermined wavelengths selected from the range of between about 1000 and about 2500 nm, said predetermined wavelengths being effective to be selectively absorbed by a preselected component of said tissue,
   b) collecting the light at said predetermined wavelengths that is not absorbed from said tissue portions,
   c) examining the amounts of absorbance of said light as determined from the collected amounts not absorbed by said illuminated body tissue, and
   d) discriminating one illuminated tissue component from an other illuminated tissue component at said wavelengths, by i) converting said absorbance amounts into second derivative values, ii) solving a disease index equation using said second derivative values to produce a solved disease index value, and iii) comparing said solved disease index value against a threshold value for diseased conditions of said tissues, whereby certain illuminated portions of body tissue are identified and located.

13. A method of treating diseased but not healthy tissue in a body vessel, comprising the steps of
   i) detecting which portions are diseased and which are healthy by the steps of claim 12 and
   ii) treating only the diseased portions.

14. A method as defined in claim 13 wherein said treating step ii) comprises exposing the diseased portions to laser light at a dosage that is proportional to the certainty determined by said detecting step i) that said exposed portions are diseased.

15. A method as defined in claim 12 wherein said step a) comprises the steps of illuminating at wavelengths selectively absorbed by preselected disease components of said tissue, and said step d) discriminates diseased tissue from healthy tissue.

16. A method as defined in claim 15 wherein said wavelengths are selectively absorbed by cholesterol esters and said body tissues are cardiovascular tissues.

17. A method as defined in claim 16 wherein said wavelengths are selected from between 1660 nm and about 1740 nm.

18. A method as defined in claim 12 wherein said step a) comprises illuminating said body tissue at two predetermined wavelengths $\lambda_1$ and $\lambda_2$ within said 1000-2500 $\mu$m range,
and said step d) comprises calculating y from the equation:

$$y = C_0 + C_1 A(\lambda_1) + C_2 A(\lambda_2)$$

wherein $A(\lambda_1) + A(\lambda_2)$ are the absorbances or the first or second derivatives of the absorbances of said tissue at said two predetermined wavelengths, and $C_0$, $C_1$ and $C_2$ are predetermined constants, and comparing the calculated y value against a predetermined threshold value.

19. A method as defined in claim 18 wherein said equation is $$y = -158.77 - 3.72 \times 10^6 A(\lambda_1) + 2.03 \times 10^6 A(\lambda_2).$$

20. A surgical instrument suitable for atherosclerosis treatment, comprising a catheter having
   a distal end constructed to penetrate a blood vessel,
   a proximal end constructed to remain outside the blood vessel,
   and a body portion connecting said ends,
   said ends and body portion including at least one optical fiber capable of delivering from one end, illumination light of desired wavelengths,
   said distal end further including optical means for transmitting and receiving light energy from said fibers to a blood vessel, and from the illuminated blood vessel to said fibers, respectively;
   said proximal end further including a) means for generating light energy at predetermined wavelengths between about 1660 nm and about 1740 nm, b) means for delivering said generated energy to said at least one fiber, c) means for detecting the amount of such generated energy that is not absorbed by illuminated tissue in a blood vessel, and d) means for discriminating illuminated healthy tissue from illuminated diseased tissue at said wavelengths, using the equation $$y = C_0 + C_1 A(\lambda_1) + C_2 A(\lambda_2) + \ldots C_n A(\lambda_n)$$

wherein $A(\lambda_1)$, $A(\lambda_2)$ and $A(\lambda_n)$ are the absorbances or the first or second derivatives of the absorbances of said tissue at n predetermined wavelengths, and $C_0$, $C_1$, $C_2$ and $C_n$ are predetermined constants, said discriminating means being effective to compare the calculated y value against a predetermined threshold value,
   said instrument further including treating means for selectively treating only the illuminated diseased tissue as determined by said discriminating means.

* * * * *

UNITED STATES PATENT AND TRADEMARK OFFICE
CERTIFICATE OF CORRECTION

PATENT NO. : 5,197,470
DATED : March 30, 1993
INVENTOR(S) : Jeffrey L. Helfer et al It is certified that error appears in the above-indentified patent and that said Letters Patent is hereby corrected as shown below:

Column 14, line 68, after "tissues", delete "." and insert therefor --,--.

Signed and Sealed this

Fifteenth Day of March, 1994

Attest:

BRUCE LEHMAN

*Attesting Officer*     *Commissioner of Patents and Trademarks*